US012220232B2

(12) United States Patent
Lee et al.

(10) Patent No.: US 12,220,232 B2
(45) Date of Patent: Feb. 11, 2025

(54) APPARATUS FOR CONTROLLING OPERATIONS OF CONTINUOUS GLUCOSE MONITORING SYSTEM

(71) Applicant: I-SENS, INC., Seoul (KR)

(72) Inventors: Jin Won Lee, Seoul (KR); Choong Beom You, Seoul (KR); Hyo Seon Park, Seoul (KR); Ha Na Lee, Seoul (KR)

(73) Assignee: I-SENS, INC., Seoul (KR)

( * ) Notice: Subject to any disclaimer, the term of this patent is extended or adjusted under 35 U.S.C. 154(b) by 960 days.

(21) Appl. No.: 17/264,796

(22) PCT Filed: Jun. 21, 2019

(86) PCT No.: PCT/KR2019/007511
§ 371 (c)(1),
(2) Date: Jan. 30, 2021

(87) PCT Pub. No.: WO2020/032382
PCT Pub. Date: Feb. 13, 2020

(65) Prior Publication Data
US 2021/0290118 A1 Sep. 23, 2021

(30) Foreign Application Priority Data

Aug. 7, 2018 (KR) .................... 10-2018-0091868

(51) Int. Cl.
*A61B 5/145* (2006.01)
*A61B 5/00* (2006.01)
(52) U.S. Cl.
CPC .......... *A61B 5/14532* (2013.01); *A61B 5/002* (2013.01); *A61B 2560/0214* (2013.01)
(58) Field of Classification Search
CPC ................................................. A61B 5/14532
See application file for complete search history.

(56) References Cited

U.S. PATENT DOCUMENTS 9,782,082 B2   10/2017 Gannon et al.
2010/0198034 A1  8/2010 Thomas et al.
(Continued)

FOREIGN PATENT DOCUMENTS

CN      205232211     5/2016
JP      2012-123552   6/2012
(Continued)

OTHER PUBLICATIONS

International Preliminary Report on Patentability (Chapter I) for PCT/KR2019/007511 issued on Feb. 9, 2021 and its English translation from WIPO (now published as WO2020/032382).
(Continued)

*Primary Examiner* — Hsinchun Liao
(74) *Attorney, Agent, or Firm* — WOMBLE BOND DICKINSON (US) LLP

(57) ABSTRACT

An apparatus for controlling operations of a continuous glucose monitoring system. When a continuous glucose monitoring system is located within a certain distance from a user terminal, power of a battery is supplied to the continuous glucose monitoring system through a power switch switched on by an enable signal generated by a near field communication module, thereby operating the continuous glucose monitoring system without user intervention. The near field communication module provides connection information to the user terminal, thereby automatically performing a pairing connection with the user terminal using the near field communication module and a bluetooth communication module. When the pairing connection with the user terminal is completed, an enable signal generated by the bluetooth communication module is provided to the power switch, thereby maintaining the pairing connection with the user terminal even when the user terminal is outside of range for near field communication.

11 Claims, 5 Drawing Sheets

(56) References Cited

U.S. PATENT DOCUMENTS

| | | | |
|---|---|---|---|
| 2012/0156993 A1* | 6/2012 | Seo | G06F 13/4045 |
| | | | 455/554.2 |
| 2014/0138432 A1 | 5/2014 | Park et al. | |
| 2014/0253323 A1* | 9/2014 | Berven | G08B 21/02 |
| | | | 340/539.12 |
| 2014/0273824 A1 | 9/2014 | Fenner et al. | |
| 2016/0210099 A1* | 7/2016 | Hampapuram | A61B 5/0004 |
| 2017/0091412 A1 | 3/2017 | Johnson | |
| 2017/0126070 A1 | 5/2017 | Lee et al. | |
| 2017/0331524 A1 | 11/2017 | Aranyosi et al. | |
| 2018/0026678 A1* | 1/2018 | Biederman | A61B 5/14532 |
| | | | 455/41.1 |
| 2018/0027106 A1 | 1/2018 | Mandapaka et al. | |
| 2018/0060529 A1 | 3/2018 | Crothall et al. | |

FOREIGN PATENT DOCUMENTS

| | | |
|---|---|---|
| JP | 2013-176579 | 9/2013 |
| JP | 2016-505808 | 2/2016 |
| JP | 2016-520379 | 7/2016 |
| JP | 2016-139917 | 8/2016 |
| KR | 10-2016-0066930 | 6/2016 |
| KR | 10-2016-0070924 | 6/2016 |
| KR | 10-2017-0051134 | 5/2017 |
| KR | 10-2018-0051215 | 5/2018 |
| WO | 2006/114297 | 11/2006 |
| WO | 2011/119896 | 9/2011 |
| WO | 2018/022235 | 2/2018 |
| WO | 2018/125841 | 7/2018 |

OTHER PUBLICATIONS

Office Action mailed on Nov. 15, 2021 for Australian Patent Application No. 2019318970.
Extended European Search Report mailed on Mar. 1, 2021for European Patent Application No. 19845690.7.
International Search Report for PCT/KR2019/007511 mailed on Sep. 23, 2019 and its English translation from WIPO (now published as WO2020/032382).
Written Opinion of the International Searching Authority for PCT/KR2019/007511 mailed on Sep. 23, 2019 and its English translation by Google Translate (now published as WO2020/032382).
Office Action mailed on Mar. 15, 2022 for Japanese Patent Application No. 2021- 506293 and its English translation provided from Global Dossier.
Office Action mailed on Feb. 14, 2022 for New Zealand Patent Application No. 773218.
Office Action dated Jun. 4, 2024 for Japanese Patent Application No. 2023-003164 and its English translation provided by Applicant's foreign counsel.
Examination Report No. 1 dated Apr. 19, 2024 for Australian Patent Application No. 2022231711.

* cited by examiner

FIG. 5
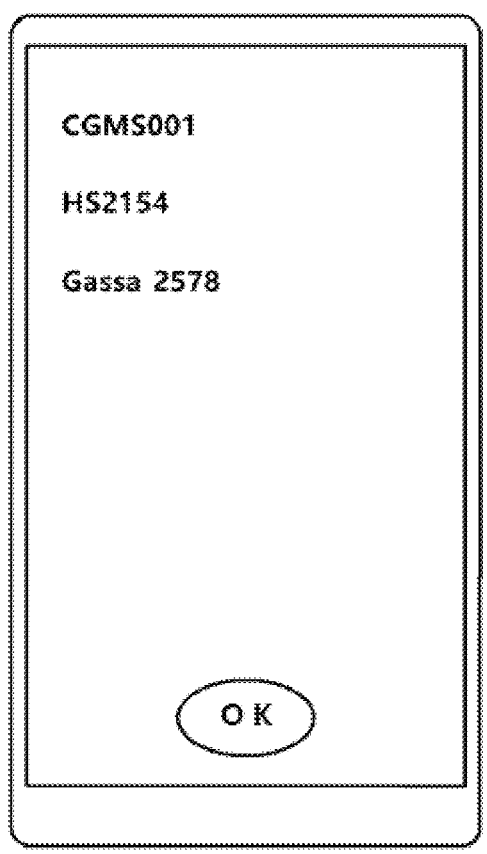
(a)
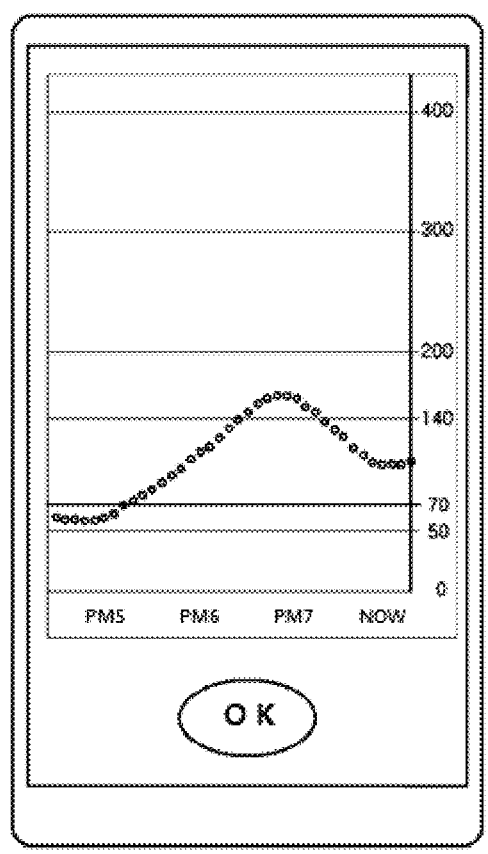
(b)

APPARATUS FOR CONTROLLING OPERATIONS OF CONTINUOUS GLUCOSE MONITORING SYSTEM

CROSS-REFERENCE TO RELATED APPLICATIONS

The present application is the U.S. National Phase of PCT Application No. PCT/KR2019/007511 filed on Jun. 21, 2019, which claims the priority to Korean Patent Application No. 10-2018-0091868 filed on Aug. 7, 2018, the entire contents of which are incorporated herein by reference.

BACKGROUND

Field

The present disclosure relates to an apparatus for controlling operations of a continuous glucose monitoring system. More specifically, in the apparatus for controlling operations of the continuous glucose monitoring system, when a continuous glucose monitoring system is located within a certain distance of a user terminal, power of a battery can be supplied to the continuous glucose monitoring system through a power switch switched on in response to an enable signal generated by a near field communication module, thereby starting operations of the continuous glucose monitoring system without user intervention. The near field communication module can provide connection information to the user terminal, thereby automatically performing a pairing connection with the user terminal using the near field communication module and a bluetooth communication module. When the pairing connection with the user terminal is completed, an enable signal generated by the bluetooth communication module can be provided to the power switch, thereby maintaining the pairing connection with the user terminal, even when the user terminal is outside of a range for near field communication.

Description

Diabetes is a chronic disease common in modern people. In the Republic of Korea, two million or more people, about 5% of the total population, suffer from diabetes.

Diabetes is caused by the pancreas producing an entirely, or relatively, insufficient amount of insulin due to a variety of reasons, such as obesity, stress, and bad eating habits, and due to congenital or hereditary reasons, so that glucose levels are absolutely high in blood, instead of being balanced in blood.

Blood contains a certain concentration of glucose, from which tissue cells produce energy.

However, when glucose levels are higher than normal, glucose is not stored appropriately in the liver, muscles, or fat cells and excessive amounts of glucose remain in the blood. Thus, diabetic patients commonly have higher blood glucose levels than other people. Excessive amounts of blood glucose may be discharged in urine without being absorbed by body tissues. Accordingly, since the body tissues may fail to have sufficient amounts of glucose, necessary for normal functioning, the body tissues may malfunction.

Diabetes has subtle or no subjective symptoms in the early stages of the disease. With the progression of the disease, however, the classic symptoms of diabetes, such as polydipsia, polyphagia, polyuria, weight loss, fatigue, itchy skin, and slow healing of cuts of the hands and feet, appear. Prolonged diabetes may cause complications, such as blurred vision, high blood pressure, nephropathy, palsy, periodontal diseases, muscle spasms, neuralgia, and gangrene.

In order to diagnose and manage diabetes such that complications do not arise, systematic measurement of blood glucose should be carried out in concert with systematic treatment.

For diabetic patients and people having higher blood glucose levels than normal, even though diabetes has not yet occurred, a number of medical device manufacturers provide various glucose monitoring systems such that blood glucose can be measured at home.

The glucose monitoring device uses a method in which a user draws blood from a finger tip and performs a blood glucose measurement once and a method in which the glucose monitoring system is attached to a user's abdomen and arm and blood glucose measurement is continuously performed.

Diabetic patients usually go through hyperglycemia and hypoglycemia. Emergencies may arise from the hypoglycemia, and diabetic patients may lose consciousness or even lose their life when hypoglycemia persists for an extended period of time without sugar supply. Therefore, immediate detection of hypoglycemia is very important for diabetic patients, but invasive glucose monitoring devices that intermittently measure blood glucose have limitations in accurately detecting hypoglycemia.

Recently, in order to overcome such limitations, continuous glucose monitoring systems (CGMSs) have been developed, which are inserted into the human body to measure a blood glucose level at an interval of several minutes, thereby assisting diabetic patients in managing and coping with emergency situations.

Invasive glucose monitoring systems measure blood glucose through a method in which a diabetic patient collects blood by stabbing a pain-sensitive finger tip with a needle to check blood glucose thereof, which may causes pain and repulsion when blood is collected. In order to minimize pain and repulsion, research and development are being conducted into CGMSs that continuously measure blood glucose after a needle-shaped sensor is inserted into a part of the abdomen, the arm, or the like which is relatively less sensitive to pain.

The CGMS includes a sensor module attached to the skin of the body to extract a body fluid and measure blood glucose and a transmitter configured to transmit a blood glucose level measured by the sensor module to a user terminal. The user terminal is provided with a dedicated application program for managing blood glucose information received from the CGMS. A user may check the measured blood glucose information through the dedicated application program of the user terminal.

In order to receive the blood glucose information and check the received blood glucose information through the user terminal, a process for establishing communication channel between the CGMS and the user terminal should be primarily performed. Typically, the user terminal and the CGMS are paired and connected using Bluetooth communication and then communicate with each other.

The CGMS has the expiration date about two weeks. In order to pair and connect the CGMS to the user terminal, a user should directly input pairing connection information to the user terminal every time. Furthermore, in the case of a user such as a senior citizen or an infant who is unfamiliar with a process of pairing and connecting the user terminal and the CGMS, due to an inexperience in operations, it may be difficult for the user to accurately measure blood glucose information or the user may not be able to measure blood glucose information during a set period due to limited battery power.

BRIEF SUMMARY

Various aspects of the present disclosure provide an apparatus for controlling operations of a continuous glucose monitoring system. When a continuous glucose monitoring system is located within a certain distance of a user terminal, power of a battery can be supplied to the continuous glucose monitoring system through a power switch switched on in response to an enable signal generated by a near field communication module, thereby starting operation of the continuous glucose monitoring system.

Also provided is an apparatus for controlling operations of a continuous glucose monitoring system, the apparatus being able to automatically perform a pairing connection with a user terminal using a near field communication module and a bluetooth communication module.

Also provided is an apparatus for controlling operations of a continuous glucose monitoring system, the apparatus being able to maintain a pairing communication with a user terminal by providing an enable signal generated by a bluetooth communication module to a power switch when the pairing connection with the user terminal is completed.

According to an aspect, an apparatus for controlling operations of a continuous glucose monitoring system may include: a near field wireless communication (NFC) module generating a first enable signal when power is supplied from a user terminal; a Bluetooth communication module; and a power switch switched on when the first enable signal is received from the NFC module and supplying power from a battery to the Bluetooth communication module, wherein the Bluetooth communication module transmits an advertising message to the user terminal when the power is supplied from the battery through the power switch.

As set forth above, the Bluetooth communication module may be activated in response to a connection signal provided through the NFC module and may transmit the advertising message to the user terminal.

As set forth above, the connection signal may be received from the user terminal through the NFC module.

As set forth above, after the connection signal is transmitted to the Bluetooth communication module, the NFC module may transmit connection information to the user terminal.

As set forth above, after the connection signal is provided to the Bluetooth communication module, the NFC module may transmit the connection information provided from the Bluetooth communication module to the user terminal.

As set forth above, a connection complete signal is received from the user terminal, the Bluetooth communication module may maintain communication with the user terminal.

As set forth above, when the connection complete message is received from the user terminal, the Bluetooth communication module may generate a second enable signal and may provide the generated second enable signal to the power switch.

As set forth above, when at least one of the first enable signal, the second enable signal, or a combination thereof, is received, the power switch may be switched on to supply the power of the battery to the Bluetooth communication module.

The apparatus for controlling operations of a continuous glucose monitoring system according to the present disclosure has the following effects.

First, according to the apparatus for controlling operations of a continuous glucose monitoring system according to the present disclosure, when a continuous glucose monitoring system is located within a certain distance from a user terminal, power of the battery can be supplied to the continuous glucose monitoring system through the power switch switched on in response to an enable signal generated by the near field communication module, thereby starting operations of the continuous glucose monitoring system without separate user intervention.

Second, in the apparatus for controlling operations of a continuous glucose monitoring system according to the present disclosure, the near field communication module provides connection information to a user terminal, a pairing connection with the user terminal is automatically performed using the near field communication module and the Bluetooth communication module.

Third, in the apparatus for controlling operations of a continuous glucose monitoring system according to the present disclosure, when a pairing connection with a user terminal is completed, an enable signal generated by the Bluetooth communication module can be provided to the power switch, thereby maintaining the pairing connection with the user terminal even when the user terminal is out of a distance for short range communication.

Fourth, in the apparatus for controlling operations of a continuous glucose monitoring system according to the present disclosure, when a user terminal is located at a short distance from a continuous glucose monitoring system, a pairing connection can be performed by transmitting connection information to the user terminal. Accordingly, information of the continuous glucose monitoring system can be transmitted only to a limited user terminal, thereby safely protecting user's personal information.

DESCRIPTION OF DRAWINGS

The above and other objects, features, and advantages of the present disclosure will be more clearly understood from the following detailed description, taken in conjunction with the accompanying drawings, in which:

FIG. 5 is a set of diagrams illustrating operation examples of a dedicated application program of a user terminal in the continuous blood glucose measurement system according to the present disclosure.

DETAILED DESCRIPTION

Figure 1:
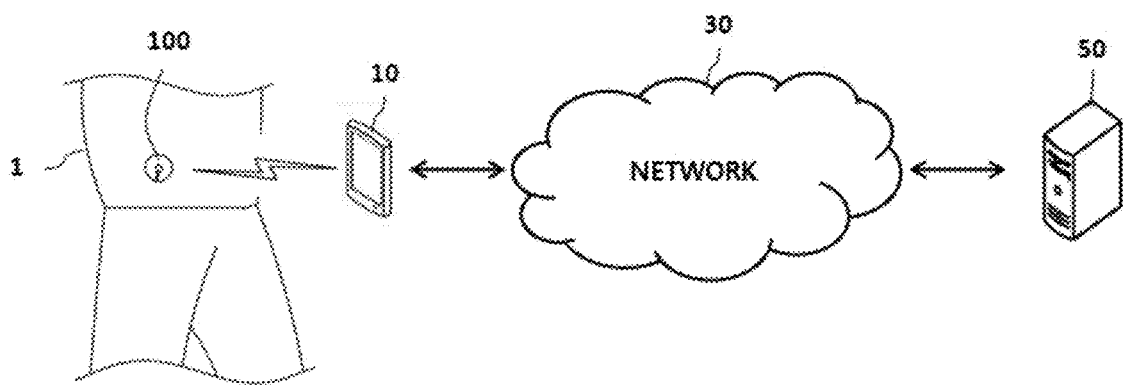
FIG. 1 is a diagram illustrating a continuous glucose monitoring system according to the present disclosure.

FIG. 1 is a diagram illustrating a continuous glucose monitoring system.

Described in more detail with reference to FIG. 1, a continuous glucose monitoring system 100 is attached to a skin of a user 1 to periodically extract a body fluid of the user 1 and continuously measure bioinformation of the user 1, for example, a blood glucose level using the extracted body fluid.

The continuous glucose monitoring system 100 and a user terminal 10 are connected to each other through short range communication, such as bluetooth communication or near field communication (NFC), to transmit and receive data through the short range communication. That is, when the continuous glucose monitoring system 100 and the user terminal 10 are located within a range of the short range communication, the continuous glucose monitoring system 100 transmits measured bioinformation of the user 1 to the user terminal 10. Hereinafter, biometric information measured in the continuous glucose monitoring system 100 will be described by exemplifying blood glucose information.

More specifically, when the user terminal 10 is adjacent to the continuous glucose monitoring system 100, an NFC module (not shown) provided in the continuous glucose monitoring system 100 starts to be operated by receiving power from the user terminal 10. The operated NFC module starts to operate a bluetooth communication module (not shown) provided in the continuous glucose monitoring system 100. The continuous glucose monitoring system 100 automatically performs a communication connection procedure using the NFC module and the bluetooth communication module to be connected to and communicate with the user terminal 10. When the user terminal 10 and the continuous glucose monitoring system 100 are connected to each other, the continuous glucose monitoring system 100 periodically transmits measured blood glucose information of the user to the user terminal 10.

Here, the user terminal 10 is a device capable of storing or outputting the blood glucose information of the user 1 received from the continuous glucose monitoring system 100 such that the blood glucose information may be checked and output to the user. A dedicated application program for managing blood glucose information may be executed in the user terminal 10. As an example of such a user terminal 10, a smartphone, a notebook, a personal digital assistant (PDA), a blood glucose management dedicated terminal, or the like may be used.

The user terminal 10 and a management server 50 are connected to each other via a network 30. The user terminal 10 transmits the blood glucose information of the user 1, received from the continuous glucose monitoring system 100, to the management server 50 or transmits sensor use information of the continuous glucose monitoring system 100 to the management server 50.

Particularly, the user terminal 10 identifies a user on the basis of inputted user information and registers the received blood glucose information by mapping the received blood glucose information to the identified user. In addition, the user terminal 10 transmits the registered blood glucose information, mapped to the user, or transmits the sensor use information to the management server 50 together with the user information.

Figure 2:
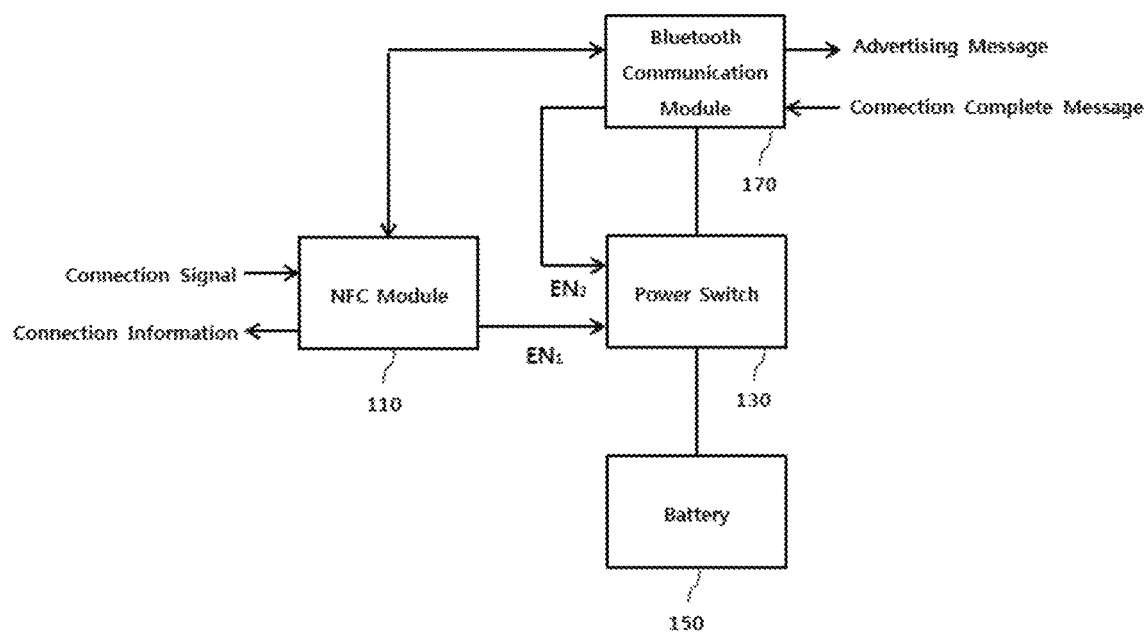
FIG. 2 is a functional block diagram illustrating an apparatus for controlling operations of a continuous glucose monitoring system according to the present disclosure.

FIG. 2 is a functional block diagram illustrating an apparatus for controlling operations of a continuous glucose monitoring system according to the present disclosure.

Described in more detail with reference to FIG. 2, when an NFC module 110 is located within a first distance at which the NFC module 110 may communicate with a user terminal, the NFC module 110 of a continuous glucose monitoring system receives operating power from the user terminal. The NFC communication module 110 receiving the operation power generates a first enable signal EN1 and provides the first enable signal EN1 to a power switch 130.

When the operating power is not received from the user terminal, the NFC module 110 does not generate an enable signal. Only when the operating power is received from the user terminal, does the NFC module 110 generate the first enable signal EN1.

The power switch 130 controls connection between a battery 150 and a bluetooth communication module 170 in response to a signal input to an enable terminal (not shown). When the first enable signal EN1 generated from the NFC module 110 is not inputted into the enable terminal, the power switch 130 maintains a switched off state. When the first enable signal EN1 generated from the NFC module 110 is inputted into the enable terminal, the power switch 130 is switched on to connect the battery 150 and the bluetooth communication module 170 to each other. When the battery 150 and the bluetooth communication module 170 are connected to each other through the power switch 130, power is supplied from the battery 150 to the bluetooth communication module 170.

When the power is supplied from the battery 150 to the bluetooth communication module 170, the bluetooth communication module 170 starts to be operated. The bluetooth communication module 170 first transmits an advertising message including an identifier of the continuous glucose monitoring system to the user terminal. After the bluetooth communication module 170 transmits the advertising message, the bluetooth communication module 170 controls the NFC module 110 to transmit connection information, for example, a pin code necessary for pairing and connecting the user terminal and the continuous glucose monitoring system to the user terminal.

When the pairing connection between the user terminal and the continuous glucose monitoring system is completed, the bluetooth communication module 170 receives a connection complete message from the user terminal. When the bluetooth communication module 170 receives the connection complete message, the bluetooth communication module 170 generates a second enable signal and provides the generated second enable signal to an enable terminal of the power switch 130.

When the NFC module 110 of the continuous glucose monitoring system does not receive power from the user terminal, due to the distance between the user terminal and the continuous glucose monitoring system being greater than the first distance and, the NFC module 110 stops generating the first enable signal EN1. When the power switch 130 receives at least one of the first enable signal EN1 and the second enable signal EN2 through the enable terminal, the power switch 130 is switched on to connect the battery 150 and the bluetooth communication module 170 to each other. After the pairing connection between the user terminal and the continuous glucose monitoring system is completed, the bluetooth communication module 170 may generate the second enable signal EN2 and may provide the second enable signal EN2 to an enable terminal of the NFC module 110. Thus, even when the distance between the user terminal and the continuous glucose monitoring system is out of the first distance, the power of the battery 150 may be continuously supplied to the bluetooth communication module 170.

Figure 3:
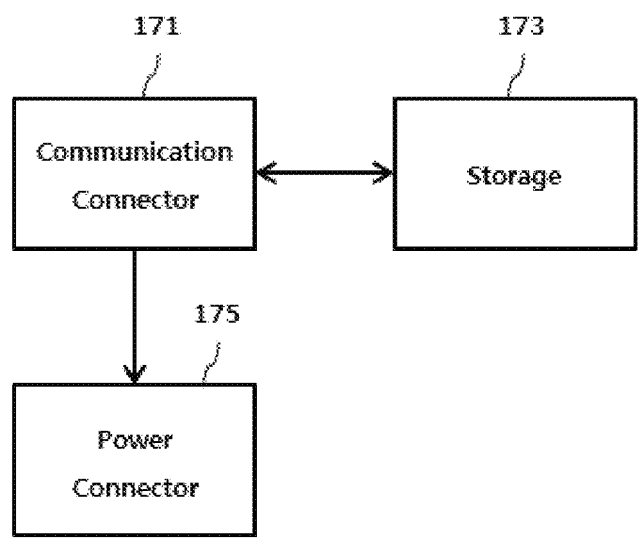
FIG. 3 is a functional block diagram illustrating an example of a Bluetooth communication module according to the present disclosure.

FIG. 3 is a functional block diagram illustrating an example of the bluetooth communication module 170 according to the present disclosure.

Described in more detail with reference to FIG. 3, when a connection signal is received from the user terminal through the NFC module, a communication connector 171 generates an advertising message and transmits the advertising message to the user terminal. The communication connector 171 generates the advertising message by providing an identifier of the continuous glucose monitoring system stored in a storage 173.

After the communication connector 171 transmits the advertising message, the communication connector 171 extracts connection information, such as a connection pin code of the continuous glucose monitoring system, stored in the storage 173, and transmits the extracted connection information to the user terminal through the NFC module. The user terminal and the continuous glucose monitoring system are automatically paired and connected using the identifier of the continuous glucose monitoring system and the connection information. When the communication connector 171 receives a connection complete message from the user terminal, the communication connector 171 transmits connection complete information to a power connector 175.

When the power connector 175 receives the connection complete information from the communication connector 171, the power connector 175 generates the second enable signal EN2 and provides the generated second enable signal EN2 to the enable terminal of the power switch.

Figure 4:
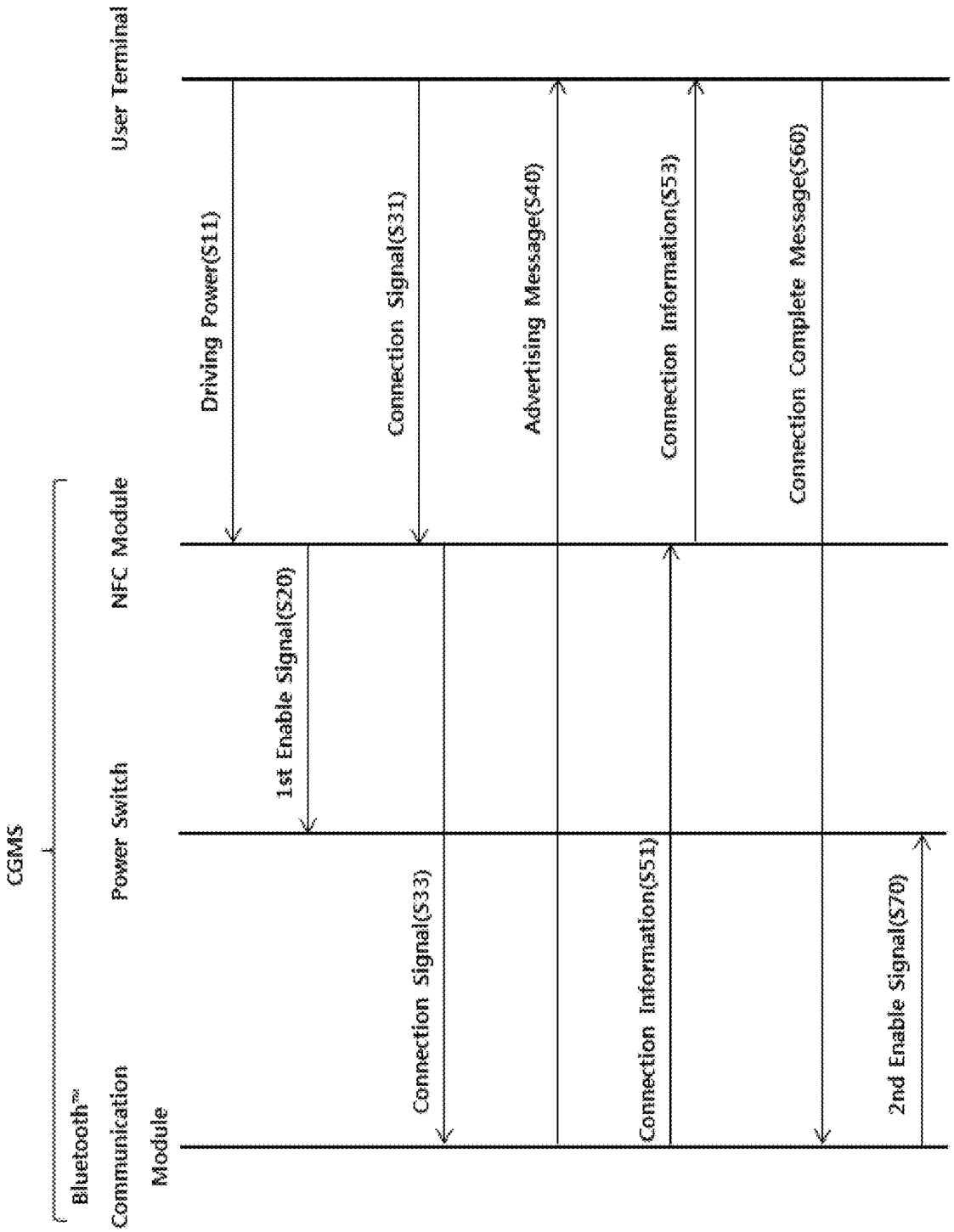
FIG. 4 is a flow diagram illustrating messages transmitted and received in the continuous glucose monitoring system according to the present disclosure.

FIG. 4 is a flow diagram illustrating messages transmitted and received in the continuous glucose monitoring system according to the present disclosure.

Described in more detail with reference to FIG. 4, when the user terminal and the continuous glucose monitoring system are located within the first distance, the NFC module receives operating power from the user terminal in S10. An NFC module is also provided in the user terminal.

The NFC module receiving the operating power from the user terminal starts to be operated, generates a first enable signal, and provides the generated first enable signal to the power switch in S20.

The power switch is switched on in response to the first enable signal and provides power of the battery to the bluetooth communication module. The bluetooth communication module receives a connection signal from the user terminal through the NFC module in S31 and S33. Here, when the user terminal and the NFC module start communicating with each other, the connection signal is generated in a dedicated application program of the user terminal and is provided to the continuous glucose monitoring system to start a pairing connection between the user terminal and the continuous glucose monitoring system.

The bluetooth communication module generates an advertising message including an identifier of the continuous glucose monitoring system in response to the connection signal and transmits the generated advertising message to the user terminal in S40. After the bluetooth communication module transmits the advertising message to the user terminal, the bluetooth communication module transmits connection information to the user terminal through the NFC module in S51 and S53. A user may confirm the continuous glucose monitoring system displayed on the user terminal, on the basis of the advertising message, and may automatically perform a pairing connection using the connection information received through the NFC module.

When the bluetooth communication module receives a connection complete message from the user terminal in S60, the bluetooth communication module generates a second enable signal and provides the generated second enable signal to the power switch in S70. Until the pairing connection between the continuous glucose monitoring system and the user terminal is completed, the power switch is switched on in response to the first enable signal received from the NFC module and provides power of the battery to the bluetooth communication module. When the pairing connection between the continuous glucose monitoring system and the user terminal is completed, the power switch is switched on in response the second enable signal received from the bluetooth communication module and provides the power of the battery to the Bluetooth communication module.

FIG. 5 is a set of diagrams illustrating an example of operation of a dedicated application program of the user terminal in the continuous glucose monitoring system according to the present disclosure.

As illustrated in FIG. 5A, when an advertising message is received from the continuous glucose monitoring system, identifiers of devices, which are searched for and are connectable, are displayed on the user terminal. In the present disclosure, when an identifier of the continuous glucose monitoring system among the connectable devices is selected by a user, the continuous glucose monitoring system and the user terminal are automatically paired and connected, on the basis of a received pin code.

According to fields to which the present disclosure is applied, even though the identifier of the continuous glucose monitoring system is not selected by the user, the continuous glucose monitoring system corresponding to a received pin code, among the connectable devices, may be automatically selected, and thus, the user terminal and the continuous glucose monitoring system may be automatically paired and connected.

As illustrated in FIG. 5B, the user terminal receives periodically measured blood glucose information from the continuous glucose monitoring system and displays the received blood glucose information to the user.

What is claimed is:

1. An apparatus for controlling operations of a continuous glucose monitoring system, the apparatus comprising:
a near field wireless communication (NFC) module generating a first enable signal when power is supplied from a user terminal;
a bluetooth communication module; and
a power switch switched on and supplying power from a battery to the bluetooth communication module when the first enable signal is received from the NFC module,
wherein:
the bluetooth communication module transmits an advertising message to the user terminal when the power is supplied from the battery through the power switch,
when a connection complete signal is received from the user terminal, the bluetooth communication module maintains communication with the user terminal, and
when a connection complete message is received from the user terminal, the bluetooth communication module generates a second enable signal and provides the generated second enable signal to the power switch.

2. The apparatus according to claim 1, wherein the bluetooth communication module is activated in response to a connection signal provided through the NFC module and transmits the advertising message to the user terminal.

3. The apparatus according to claim 2, wherein the connection signal is received from the user terminal through the NFC module.

4. The apparatus according to claim 2, wherein, after the connection signal is transmitted to the bluetooth communication module, the NFC module transmits connection information to the user terminal.

5. The apparatus according to claim 4, wherein, after the connection signal is provided to the bluetooth communication module, the NFC module transmits the connection information provided from the bluetooth communication module to the user terminal.

6. The apparatus according to claim 1, wherein, when at least one of the first enable signal and the second enable signal is received, the power switch is switched on to supply the power of the battery to the bluetooth communication module.

7. An apparatus for controlling operations of a continuous glucose monitoring system, the apparatus comprising:
- a near field wireless communication (NFC) module generating a first enable signal when power is supplied from a user terminal;
- a bluetooth communication module; and
- a power switch switched on and supplying power from a battery to the bluetooth communication module when the first enable signal is received from the NFC module, wherein:
- the bluetooth communication module transmits an advertising message to the user terminal when the power is supplied from the battery through the power switch,
- the bluetooth communication module is activated in response to a connection signal provided through the NFC module and transmits the advertising message to the user terminal, and after the connection signal is provided to the bluetooth communication module, the NFC module transmits connection information provided from the bluetooth communication module to the user terminal.

8. The apparatus according to claim 7, wherein the connection signal is received from the user terminal through the NFC module.

9. The apparatus according to claim 7, wherein, when a connection complete signal is received from the user terminal, the bluetooth communication module maintains communication with the user terminal.

10. The apparatus according to claim 9, wherein, when a connection complete message is received from the user terminal, the bluetooth communication module generates a second enable signal and provides the generated second enable signal to the power switch.

11. The apparatus according to claim 10, wherein, when at least one of the first enable signal and the second enable signal is received, the power switch is switched on to supply the power of the battery to the bluetooth communication module.

* * * * *